(12) United States Patent
Gröner et al.

(10) Patent No.: US 7,382,452 B2
(45) Date of Patent: Jun. 3, 2008

(54) PARTICLE COUNTER FOR FOREIGN PARTICLES IN A FLUID STREAM

(75) Inventors: Alfred Gröner, Öhringen (DE); Markus Klotz, Bad Liebenzell (DE)

(73) Assignee: Mahle International GmbH, Stuttgart (DE)

( * ) Notice: Subject to any disclaimer, the term of this patent is extended or adjusted under 35 U.S.C. 154(b) by 105 days.

(21) Appl. No.: 11/402,073

(22) Filed: Apr. 11, 2006

(65) Prior Publication Data

US 2006/0227926 A1    Oct. 12, 2006

(30) Foreign Application Priority Data

Apr. 11, 2005    (DE) .................. 10 2005 016 761

(51) Int. Cl.
   *G01N 15/02*    (2006.01)
(52) U.S. Cl. ..................................... 356/336
(58) Field of Classification Search .............. 356/336
   See application file for complete search history.

(56) References Cited

U.S. PATENT DOCUMENTS 3,632,210 A * 1/1972 Rich ........................ 356/37
5,118,959 A * 6/1992 Caldow et al. ............. 250/573
5,379,791 A   1/1995 Christopher
2007/0056395 A1* 3/2007 Bae et al. .................. 73/865.5

FOREIGN PATENT DOCUMENTS

| DE | 2062698 | 6/1972 |
| DE | 2428466 | 1/1975 |
| DE | 8912584 | 12/1989 |
| DE | 4110231 | 10/1992 |

* cited by examiner

*Primary Examiner*—Roy M Punnoose
(74) *Attorney, Agent, or Firm*—Collard & Roe, P.C.

(57) ABSTRACT

A particle counter that operates according to the blackout and/or light blockade method for counting foreign particles in a fluid stream, in particular in a hydraulic fluid stream, has a photoelectric barrier whose beam of light penetrates through a measurement channel through which a bypass substream of the fluid stream flows and has an electronic analyzer downstream from the receiver of the photoelectric barrier. To this end, such a particle counter includes a pressure regulating device acting on the fluid stream forces a predefined pressure difference which is independent of the flow properties of the main fluid stream onto the area situated between the inlet and outlet of the measurement channel. (11), The particle counter includes a heating or cooling device for regulating the temperature of the substream flowing through the measurement channel at a predetermined temperature level.

5 Claims, 1 Drawing Sheet

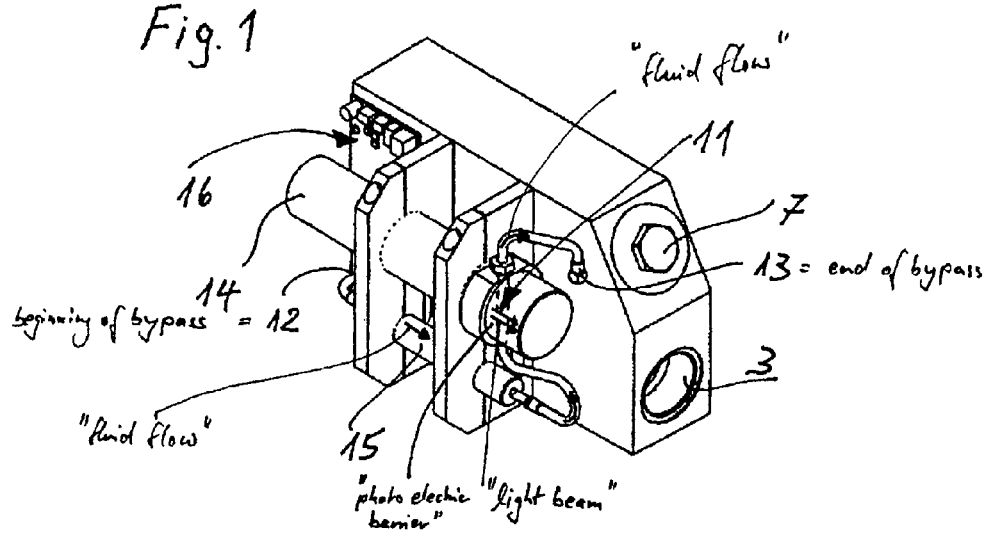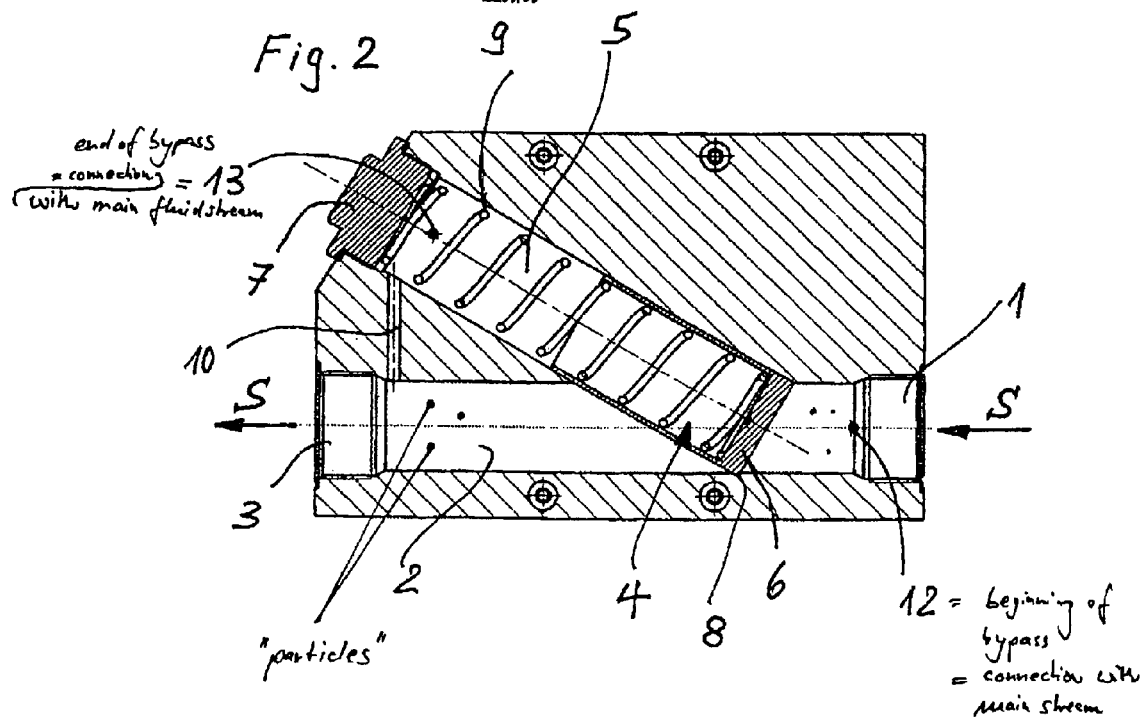

PARTICLE COUNTER FOR FOREIGN PARTICLES IN A FLUID STREAM

CROSS REFERENCE TO RELATED APPLICATIONS

Applicants claim priority under 35 U.S.C. 119 of German Patent Application No. 10 2005 016 761.6 filed Apr. 11, 2005.

BACKGROUND OF THE INVENTION

1. Field of the Invention

The present invention relates to a particle counter that operates by the blackout and/or light blockade method for counting foreign particles in a fluid stream, especially in a hydraulic fluid stream.

2. The Prior Art

Such a particle counter is known from DE 8912584 U1.

SUMMARY OF THE INVENTION

With any particle counter, a complex volume flow regulating device is necessary to achieve a constant flow rate within the measurement channel.

The present invention relates to the problem of creating a particle counter that has the simplest possible design and nevertheless operates with a high measurement accuracy. Such a particle counter is to be a component of a working device through which a liquid that is to be measured flows. This liquid should be in particular hydraulic oil in a hydraulically operating device, the degree of soiling of which can be determined in a steady state with such a particle counter, doing so in intervals as short as desired. It should also be possible to recognize different particle sizes separately. In particular, continuous monitoring of the degree of soiling of such a hydraulic fluid should be possible by using an inventive particle counter.

These problems are solved by the embodiment of a generic particle counter according to the present invention.

The invention is based on the following general idea.

To be able to perform a measurement of the number and size of particles in a fluid flowing through a measurement channel within a photoelectric barrier using a blackout method and/or a light blockade method, the volume flow per unit of time in the measurement must be known. The size of a volume flow is known by a simple method, e.g., when it is adjusted to a certain value upstream and can be kept constant. A constant volume flow is in turn necessarily obtained in a flow channel that is kept constant geometrically at a constant predetermined pressure gradient along this flow channel. However, an additional prerequisite is that the flowing liquid must have a constant viscosity. Since the viscosity of a liquid is usually dependent on temperature, especially in the case of a hydraulic fluid, a constant volume flow at a constant pressure gradient necessarily presupposes temperature equality. These two prerequisites defined above for a constant volume flow are achieved according to this invention with regard to a constant pressure drop through the use of a heating or cooling system to influence the temperature of the fluid stream to be measured by means of a pressure-reducing valve operated as a spring-loaded valve and with respect to a constant temperature. The heating or cooling device is designed so that in order to perform a measurement, the prevailing temperature is preferably outside of the possible operating range. This ensures that regardless of instantaneous operating temperatures, the measurement can always be performed at a constant measurement temperature outside of the operating temperature. As a rule, the heating device used is one by means of which measurement, i.e., active operation of a particle counter, is always performed with a liquid whose particle burden is to be measured at a temperature above the operating temperature. Through the approach according to the present invention, it is possible to eliminate the need for a volume flow regulator which would have a complex design and would often not be very accurate in measurement, such as, for example, that which must be used in the previously known state of the art according to DE 8912584 U1 cited in the introduction.

Advantageous and expedient embodiments of the present invention are the object of the subclaims and are explained in greater detail below on the basis of an exemplary embodiment. One such exemplary embodiment is illustrated in the drawing.

The inventive device may also be used to advantage in particular for measurement and monitoring the degree of soiling of transmission oil.

According to the previously described aspect of the present invention, the influence of a variable viscosity on a constant fluid stream to be created in a measurement channel based on a pressure difference is eliminated by targeted heating of the measurement fluid stream. Another possibility for preventing a variable viscosity as an interfering factor for the measurement is to determine the temperature of the measurement fluid in the measurement channel and correct the respective measured values of the particle counts by using an electronically stored correction curve determined experimentally as a function of various measurement fluid temperatures in particular. The term "correcting" as used here means that the viscosity-induced changes in volume flow of the measurement fluid stream are neutralized downstream from an electronic correction memory, whereby the correction memory is to be created with respect to a liquid on which a measurement is to be performed. Different correction values may of course be stored for different fluids to be retrieved as needed.

BRIEF DESCRIPTION OF THE DRAWINGS

The drawing shows:

FIG. 1 a perspective view of a particle counter,

FIG. 2 a section through the particle counter according to FIG. 1, showing the design of a pressure reducing valve integrated into it.

DETAILED DESCRIPTION OF PREFERRED EMBODIMENTS

The particle counter is designed as a measurement device that can be used in a fluid line, in particular a hydraulic fluid line. Incoming fluid flows in a main stream into a main flow channel opening 1 of a main flow channel 2 and leaves this main flow channel 2 through a main channel outlet opening 3.

A spring-loaded throttle valve 4 is integrated into the main flow channel 2. This throttle valve 4 includes a piston 6 which is displaceably mounted in a cylinder 5. The cylinder 5 is provided at one end with a closed bottom 7 in the form of a sealing plug and is open at the other end. From this open end of the cylinder 5, the piston 6 can penetrate into the flow path of the main flow channel 2 and can completely close this path. In the case of a complete closure, the piston 6 is in contact with a valve seat 8 arranged accordingly in the main flow channel 2. The piston 6 is acted upon by force applied by a spring 9 mounted in the interior of the cylinder 5 and acting in the direction of a closure position on the valve seat 8. The spring 9 is supported on the piston 6 at one end and on the bottom 7 of the cylinder at the other end. The axis of the cylinder 5 along which the piston 6 can move is inclined with respect to the longitudinal axis of the main flow channel 2 such that fluid flowing from the inlet opening 1 into the main flow channel 2 can act on the end face of the piston 6 to open the throttle valve. This opening force counteracts the force of the spring 9, which is designed here as a compression spring. The direction of flow of the main flow channel 2 is labeled with flow arrows S. Downstream from the piston 6 of the throttle valve 4, the main flow channel 2 is connected to the interior of the cylinder 5 through a connecting channel 10 in the form of a throttle valve, for example, in such a manner as to equalize the pressure.

Due to such a design and arrangement of the throttle valve 4, a constant pressure drop which is independent of the absolute pressure of the fluid flowing in the main flow channel 2 is created there in an extremely simple way and is reliably ensured.

The inventive photoelectric barrier measurement according to the blackout and/or light blockade method, which is sufficiently well known in the state of the art, is performed in a measurement channel 11 designed as a bypass bridging the throttle valve 4 to the main flow channel 2. FIG. 2 shows the connecting openings of this measurement channel, whereby the measurement channel inlet 12 is situated upstream from the throttle valve 4 and the measurement channel outlet is labeled as 13. A sensor device 14 which is essentially known for such a particle counter is assigned to the measurement channel 11.

Between the measurement channel inlet 12 and the photoelectric barrier area of this measurement channel 11 in the area of the sensor device 14, this measurement channel 11 passes through a heating device 15 in its inlet line area. Inside this heating device 15, the liquid flowing through it is heated to a specified temperature outside of the possible operating temperatures, so this liquid always flows through the sensor device 14 at the same constant temperature.

The electronic part of the particle counter is labeled as 16 in FIG. 1. This electronic part 16 includes the devices for a telemetric remote display, for example, of the measured values from the sensor device 14 including their measured values analyzed in this electronic part in particular. The analyzed measured values can be displayed either digitally or as analog values at any desired location in a known manner. For example, a telemetric remote display is of particular interest when using an inventive particle counter for monitoring a hydraulic oil circuit in an offshore wind power plant.

The throttle valve 4 may be designed for example in the form of a corresponding spring 9 for a constant pressure drop of 0.5 bar within the main flow channel 2. The measurement channel volume flow established in this way and on the basis of the size of the flow cross section through the measurement channel 11 may amount to 50 mL/min, for example.

A single-channel laser device, for example, may be used as the sensor device 14. The measured values that can be achieved and the possibilities for analyzing them correspond to those known in general with generic particle counters according to the state of the art, which is why details in this regard need not be given here in the description of the present invention.

However, reference should be made to the following.

With reference to the use of a particle counter in a certain liquid on which a measurement is to be performed, the measurement device must be calibrated with a test fluid that is adjusted to the liquid to be measured. This test fluid is always mixed with a precisely defined test dust.

With the inventive measurement device, it is possible to determine the particle size in a measurement window so that the analysis of the measurement results can be switched to preset classes of particle sizes by simply making a switch in the measurement device. The switching may be performed automatically by the electronic system so that a measurement device which is a single-channel device in principle can operate like a multichannel measurement device by repeatedly switching to a different measurement class. This is a particular feature of the present invention.

A measurement accuracy of at least approximately ±20% can easily be ensured when using a measurement device according to this invention.

All the features explained in the description and characterized in the following claims may be essential to the invention either individually or when combined in any desired form.

The invention claimed is:

1. A particle counter that operates according to the blackout and/or light blockade method for counting foreign particles in a fluid stream, in particular in a hydraulic fluid stream, having a photoelectric barrier whose light beam penetrates through a measurement channel through which a bypass substream of the fluid stream flows and having an electronic analyzer connected downstream from the receiver of the photoelectric barrier, comprising the features a pressure regulating device (4) that acts on the fluid stream forces a predefined pressure difference, which is independent of the flow properties of the main fluid stream, onto the region between the inlet and the outlet of the measurement channel (11), where the photoelectric barrier is located, the particle counter includes a heating or cooling device (15) for regulating the temperature of the substream flowing through the measurement channel (11) at a predetermined temperature level.

2. The particle counter according to claim 1, wherein the pressure regulating device is designed as a throttle valve (4) and has a sealing body (6) that is acted upon by spring force and is situated inside the valve throttle path, the open and closed positions of which depend on the pressure difference applied to it on the incoming flow end and on the outgoing flow end, whereby the spring force acting on the sealing body (6) counteracts the dynamic pressure exerted on the sealing body (6) on the oncoming flow end in such a manner as to act like a throttle.

3. The particle counter according to claim 2, comprising the features the sealing body is a piston (6) displaceably mounted in a cylinder (5), the cylinder (5) is bordered at one end by a fixed cylinder bottom (7) and at the other end by the displaceable piston (6), the piston (6) is immersed into the fluid stream at one end protruding out of the cylinder (5), the piston (6) is loaded by the force of a spring (9) in the direction of leaving the cylinder (5), the spring force is directed against a force acting to open the closure by oncoming fluid against the piston (6), the space of the cylinder (5) enclosed by the piston (6) is connected by a connecting channel (10) to the outflow end of the piston (6) within the fluid stream, the pressure difference applied as a constant pressure to the measurement channel (11) with the fluid flowing through it is determined by the force of the spring (9) acting upon the piston (6).

4. The particle counter according to claim 1, further comprising means for a remote display of the measured values.

5. The particle counter according to claim 4, wherein means are provided thereon for a telemetric remote display.

\* \* \* \* \*